US011007017B2

(12) United States Patent
O'Grady et al.

(10) Patent No.: US 11,007,017 B2
(45) Date of Patent: May 18, 2021

(54) METHODS AND DEVICES FOR TABLE POSE TRACKING USING FIDUCIAL MARKERS

(71) Applicant: INTUITIVE SURGICAL OPERATIONS, INC., Sunnyvale, CA (US)

(72) Inventors: Patrick O'Grady, Alameda, CA (US); Tao Zhao, Sunnyvale, CA (US); Christopher R. Burns, San Jose, CA (US); Jason Hemphill, Los Gatos, CA (US); Brian D. Hoffman, Mountain View, CA (US); Simon P. Dimaio, San Carlos, CA (US); Rodney Vance, Willow Spring, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 116 days.

(21) Appl. No.: 16/292,213

(22) Filed: Mar. 4, 2019

(65) Prior Publication Data

US 2019/0192233 A1 Jun. 27, 2019

Related U.S. Application Data

(63) Continuation of application No. 15/126,254, filed as application No. PCT/US2015/020898 on Mar. 17, 2015, now Pat. No. 10,258,414.
(Continued)

(51) Int. Cl.
*A61B 34/00* (2016.01)
*A61B 34/20* (2016.01)
(Continued)

(52) U.S. Cl.
CPC .............. *A61B 34/20* (2016.02); *A61B 34/30* (2016.02); *A61B 34/35* (2016.02); *A61B 34/37* (2016.02);
(Continued)

(58) Field of Classification Search
CPC ........... A61B 34/20; A61B 34/35; A61B 4/70; A61B 34/30; A61B 90/98; A61B 90/90;
(Continued)

(56) References Cited

U.S. PATENT DOCUMENTS

| 5,184,601 A | 2/1993 | Putman et al. |
| 5,445,166 A | 8/1995 | Taylor et al. |

(Continued)

FOREIGN PATENT DOCUMENTS

| CN | 102451040 A | 5/2012 |
| JP | 2008541966 A | 11/2008 |

(Continued)

OTHER PUBLICATIONS

Extended European Search Report for Application No. EP19201192.2 dated Nov. 28, 2019, 12 pages.

(Continued)

*Primary Examiner* — Ian Jen
(74) *Attorney, Agent, or Firm* — Haynes and Boone, LLP

(57) ABSTRACT

Methods and systems for registering a manipulator assembly and independently positionable surgical table are provided herein. In one aspect, methods include reading a fiducial marker on the surgical table with a sensor associated with the manipulator assembly and localizing the manipulator assembly and surgical table with respect to a common reference frame. Methods may further include translating a 3D configuration of the surgical table to a 2D frame of (Continued)

reference so as to estimate a 3D pose of the surgical table relative the manipulator assembly for use in coordinating movements therebetween.

15 Claims, 23 Drawing Sheets

Related U.S. Application Data

(60) Provisional application No. 61/954,559, filed on Mar. 17, 2014.

(51) Int. Cl.
| | | |
|---|---|---|
| *A61B 90/96* | (2016.01) | |
| *A61B 34/30* | (2016.01) | |
| *A61B 34/37* | (2016.01) | |
| *A61B 90/90* | (2016.01) | |
| *A61B 90/98* | (2016.01) | |
| *A61B 34/35* | (2016.01) | |
| *A61G 13/00* | (2006.01) | |
| *A61B 90/00* | (2016.01) | |

(52) U.S. Cl.
CPC .............. *A61B 34/70* (2016.02); *A61B 90/90* (2016.02); *A61B 90/96* (2016.02); *A61B 90/98* (2016.02); *A61G 13/00* (2013.01); *A61B 2034/2051* (2016.02); *A61B 2034/2057* (2016.02); *A61B 2034/2068* (2016.02); *A61B 2090/3983* (2016.02); *A61G 2205/10* (2013.01); *A61G 2205/60* (2013.01)

(58) Field of Classification Search
CPC . A61B 34/37; A61B 90/96; A61B 2090/3983; A61B 2034/2068; A61B 2034/2057; A61B 2034/2051; A61G 13/00; A61G 2205/60; A61G 2205/10
See application file for complete search history.

(56) References Cited

U.S. PATENT DOCUMENTS

| | | | |
|---|---|---|---|
| 5,800,423 | A | 9/1998 | Jensen et al. |
| 5,808,665 | A | 9/1998 | Green et al. |
| 5,855,583 | A | 1/1999 | Wang et al. |
| 6,246,200 | B1 | 6/2001 | Blumenkranz et al. |
| 6,546,277 | B1 | 4/2003 | Franck et al. |
| 6,676,669 | B2 | 1/2004 | Charles et al. |
| 6,702,805 | B1 | 3/2004 | Stuart et al. |
| 6,758,843 | B2 | 7/2004 | Jensen et al. |
| 6,788,018 | B1 | 9/2004 | Blumenkranz et al. |
| 7,594,912 | B2 | 9/2009 | Cooper et al. |
| 7,763,015 | B2 | 7/2010 | Cooper et al. |
| 9,259,282 | B2 | 2/2016 | Azizian et al. |
| 10,258,414 | B2 | 4/2019 | O'Grady |
| 2003/0007125 | A1 | 1/2003 | Levine et al. |
| 2005/0228266 | A1 | 10/2005 | McCombs |
| 2005/0279368 | A1 | 12/2005 | McCombs et al. |
| 2007/0270690 | A1 | 11/2007 | Woerlein |
| 2008/0240889 | A1 | 10/2008 | Yokoyama |
| 2008/0285724 | A1 | 11/2008 | Dehler |
| 2009/0010390 | A1 | 1/2009 | Saoudi et al. |
| 2009/0163928 | A1 | 6/2009 | Schena |
| 2010/0168562 | A1 | 7/2010 | Zhao et al. |
| 2011/0166450 | A1 | 7/2011 | Peyrard et al. |
| 2011/0264110 | A1 | 10/2011 | Nowlin et al. |
| 2012/0101508 | A1 | 4/2012 | Wook Choi et al. |
| 2012/0194514 | A1* | 8/2012 | Sakaguchi ........... H04N 13/383 345/419 |
| 2013/0193189 | A1* | 8/2013 | Swensgard ............ A61B 34/70 227/176.1 |
| 2013/0218137 | A1 | 8/2013 | Abovitz et al. |
| 2014/0049629 | A1 | 2/2014 | Siewerdsen et al. |
| 2017/0079722 | A1 | 3/2017 | O'Grady et al. |

FOREIGN PATENT DOCUMENTS

| | | |
|---|---|---|
| WO | WO-2006124390 A2 | 11/2006 |
| WO | WO-2010078009 A1 | 7/2010 |
| WO | WO-2012155050 A2 * | 11/2012 ............. A61B 6/583 |

OTHER PUBLICATIONS

International Search Report and Written Opinion for Application No. PCT/US15/20898, dated Jun. 8, 2015, 14 pages.
Extended European Search Report for Application No. 15765777.6, dated Jul. 25, 2017, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

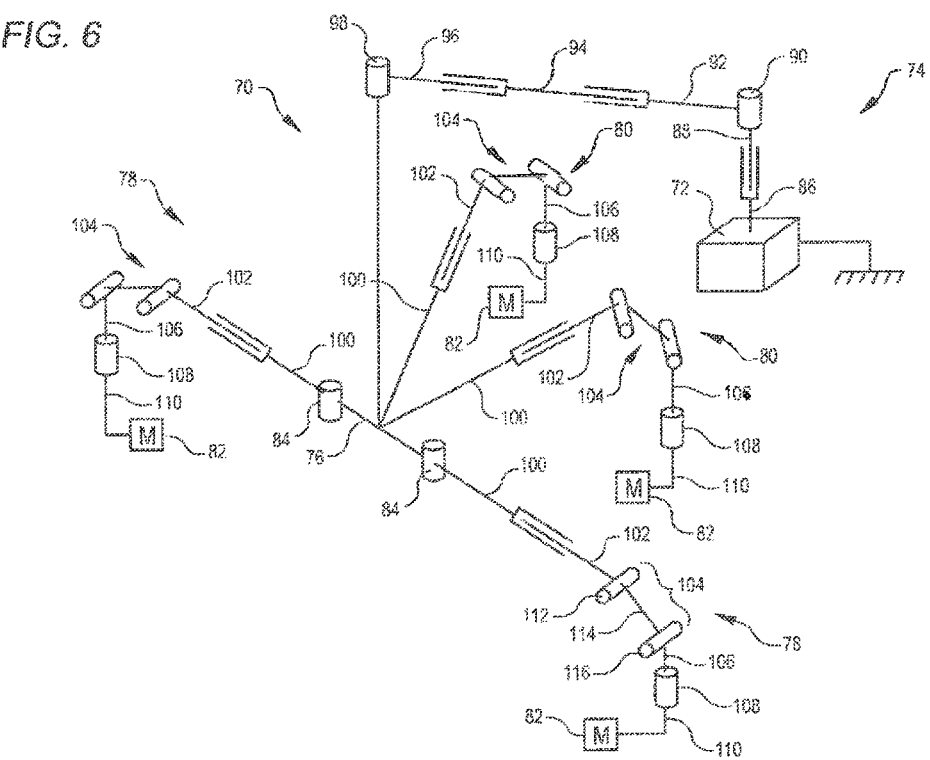

Plan view

Image view

METHODS AND DEVICES FOR TABLE POSE TRACKING USING FIDUCIAL MARKERS

RELATED APPLICATIONS

The present application is a continuation of U.S. patent application Ser. No. 15/126,254, filed Sep. 14, 2016, which is the U.S. national phase of International Application No. PCT/US2015/020898, filed Mar. 17, 2015, which designated the U.S. and claims priority to U.S. Provisional Application No. 61/954,559, filed on Mar. 17, 2014, the entire contents of each of which are incorporated herein by reference.

The present application is related to U.S. Provisional Application 61/954,538, entitled "Methods and Devices for Tele-Surgical Table Registration," filed Mar. 17, 2014, which is incorporated herein by reference.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive surgical or tele-surgical systems have been developed to increase a surgeon's dexterity and avoid some of the limitations of traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more tele-surgical arms on each of which a surgical instrument is mounted. Operative communication between master controllers and associated manipulator arm and instrument assemblies is typically achieved through a control system. The control system typically includes at least one processor that relays input commands from the master controllers to the associated manipulator arm and instrument assemblies and back from the instrument and arm assemblies to the associated master controllers in the case of, for example, force feedback or the like. One example of a tele-surgical system is the DA VINCI® system available from Intuitive Surgical, Inc. of Sunnyvale, Calif.

A variety of structural arrangements can be used to support the surgical instrument at the surgical site during tele-surgery. The driven linkage or "slave" is often called a tele-surgical manipulator, and exemplary linkage arrangements for use as a tele-surgical manipulator during minimally invasive tele-surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the tele-surgical manipulator and the surgical instrument at the surgical site during tele-surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While such new tele-surgical systems and devices have proven highly effective and advantageous, providing a wide range of configurations and coordinated movement between highly maneuverable manipulators, it can prove challenging to localize such movement in a surgical environment. Therefore, further improvements are desirable. It would be particularly beneficial if these improved technologies enhanced the efficiency and ease of use of tele-surgical systems. For example, it would be particularly beneficial to increase maneuverability, improve space utilization in an operating room, provide a faster and easier set-up, inhibit manipulator collision during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved tele-surgical devices, systems, and methods, and in particular methods and system for localization of a surgical table and estimating a table pose. Tele-surgical systems include kinematic linkage structures and associated control systems that are are particularly beneficial in performing minimally invasive surgical procedures on a patient. Such procedures often utilize interrelated and coordinated movement between multiple manipulators, each of which is highly configurable, having a range of alternative configuration for a given end effector position within the surgical environment. For various reasons, it may be desirable to position the patient in a particular position and/or orientation for a particular procedure. In addition, in some procedures, it may be further desirable to alter the position and/or orientation of the patient during a procedure. For example, certain patient positions and/or orientations may be particularly useful in accessing certain areas within the surgical workspace or it may be desirable for a patient to be disposed in particular alignments (e.g. inclined along one or more axes) during a procedure for various physiological reasons. Since many tele-surgical systems utilize a surgical table that is separate from the manipulator system and is often independently positionable along multiple degrees of freedom, various positions of the surgical table can present certain challenges during operation of tele-surgical manipulators, particularly in systems having multiple manipulators. Therefore, it would be desirable for such manipulator systems to have a means by which the surgical table can be "localized" with the manipulator assembly such that a spatial relationship between the surgical table and the manipulator assembly can be determined and utilized in calculating movement of the surgical manipulators. In one aspect, it would be desirable if such localization could be achieved without direct contact between the manipulator assembly and the surgical table.

In one aspect, the invention provides methods of localization of a surgical table using one or more fiducial markers. Methods of localization include reading one or more fiducial markers, such as 2D barcodes, disposed on a surgical table and converting a 3D pose of the surgical table to a 2D frame of reference common to the manipulator assembly and determining a spatial relationship between the surgical table and the manipulator assembly. Such methods may utilize a sensor, such as an optical sensor or camera, disposed within a base of the manipulator assembly such that when the surgical table is positioned in close proximity the surgical table can be localized relative the manipulator assembly with respect to the ground plane such that a spatial relationship between the pose of the surgical table and the manipulator assembly can be determined. This is advantageous as such pose estimation can be utilized in coordinated movements of the manipulators and the surgical table, for example, in controlled movement of the surgical table to compensate for patient movement, such as from a heartbeat or breathing, or to facilitate movement of certain organs of the patient during a procedure due to gravity.

In one aspect, methods of estimating a pose of a surgical table include: reading one or more fiducial markers on a base of the surgical table with a camera associated with a manipulator assembly adjacent the surgical table; and localizing the surgical table relative the manipulator assembly on a common plane based on the reading of the one or more markers. The one or more fiducial markers are disposed on the surgical table at various fixed locations, typically, at known and/or pre-determined locations and/or orientations relative the table. Methods may include affixing the one or more makers to the surgical table and/or forming the one or more markers in the surgical table at select locations in a particular orientation relative the surgical table. Forming the one or more markers in the surgical table may include etching, engraving and/or embossing the one or more markers in the surgical table.

In some embodiments, reading the one or more markers includes reading at least one of the one or more markers before and/or during a surgical procedure while a patient is supported on the surgical table. In one aspect, the common plane is a ground plane on which the surgical table and the manipulator assembly are disposed. In many embodiments, the surgical table is positionable along one or more degrees of freedom (DOF).

In some aspects, the method includes translating a 6 DOF 3D pose of the positionable surgical table to a 3DOF 2D pose on the common plane and estimating a 3D pose of the surgical table relative the manipulator assembly based on localization of the base of the surgical table relative to the manipulator assembly on the common plane. In some embodiments, the methods may include extracting locations of the surgical table within a visual image obtained with the camera and providing a representation or indication of the surgical table with respect to a camera view of the camera.

In another aspect, the methods may include reading the one or more markers and identifying a type, model, or make of surgical table based on reading of marker. Compatibility between table and manipulator assembly can then be checked and/or granting of permissions for use of manipulator assembly with surgical table.

In some embodiments, the one or more markers are a plurality of markers disposed at multiple locations on the surgical table and reading the one or more markers includes reading at least one of the one or more markers. In one aspect, reading the one or more markers comprises reading a single marker of the one or more markers and wherein localization of the surgical table is based on the reading of the single marker.

In another aspect, the methods include reading at least one of the one or more markers subsequent the initial reading of the one or more markers and localization based on the initial reading; and localizing the surgical table relative the manipulator assembly on the common plane based on the subsequent reading of the one or more markers so as to update and/or verify initial localization.

In one aspect, the invention provides tele-surgical systems that include a manipulator assembly, a surgical table disposed in proximity to the manipulator assembly, the surgical table having one or more fiducial markers; and a sensor that is configured to read the one or more markers of the surgical table when the surgical table is positioned within close proximity of the manipulator assembly. In some embodiments, the surgical table is positionable along one or more DOF. The sensor may include a camera associated with the manipulator assembly. In some embodiments, the one or more fiducial markers may include a barcode, an RFID tag, a light, or any combination thereof. The one or more markers may be fixedly attached and/or formed in select portions of the surgical table. In one aspect, the one are fixedly attached and/or formed in select portions and locations in a particular orientation relative the surgical table such that a pose of the table relative a ground plane is determinable from reading of at least one of the one or more markers. In some embodiments, the one or more fiducial markers comprise one or more 2D barcodes extending about a base of the surgical table and/or along an edge or side of a surgical table top of the surgical table.

In another aspect, the system includes a processor configured to: read one or more markers on a base of the surgical table with a camera associated with a manipulator assembly adjacent the surgical table; and localize the surgical table relative the manipulator assembly on a common plane based on the reading of the one or more markers. In some embodiments, where the surgical table is positionable along 6 DOF and the processor is further configured to: translate a 6 DOF 3D pose of the positionable surgical table to a 3DOF 2D pose on the common plane. The processor may further be configured to estimate a 3D pose of the surgical table relative the manipulator assembly based on localization of the base of the surgical table relative to the manipulator assembly on the common plane. In some embodiments, the processor is further configured to: extract locations of the surgical table within a visual image obtained with the sensor, and provide a representation or indication of the surgical table with respect to a camera view of the camera. In some embodiments, the processor is further configured to: identify a type, model, or make of surgical table based on reading of marker. The processor may be configured to check a compatibility aspect between table and manipulator assembly and/or granting permissions for use of manipulator assembly with surgical table based on such an identification.

In another aspect, the invention provides a table, typically a surgical table for use in tele-surgical system. In some embodiments, the table includes a substrate having a patient support surface; a support structure supporting the substrate, the support structure being movable such that the patient support surface is positionable along one or more DOF; and one or more fiducial makers disposed on surgical table at select locations and/or orientations such that a pose of the surgical table relative a ground plane is determinable by reading of the one or more markers. The one or more markers may include a plurality of markers disposed along an outer edge or side of the substrate and/or a base of the surgical table. In some embodiments, the one or more markers are disposed at select locations and/or orientations are pre-determined such that the pose of the table is determinable by reading of at least one of the one or more markers. In one aspect, the support structure is configured such that the table substrate is positionable along multiple DOF, for example 6 DOF, and the one or more markers may include a series of 2D barcodes extending about the surgical table.

In some embodiments, the table includes a sensor that is configured to read the one or more markers of the surgical table when the surgical table is positioned and being communicatively coupled with a tele-surgical system having a manipulator assembly. In other embodiments, the sensor is associated with another device external to the table, such as a manipulator assembly. The sensor may be a photo-sensitive detector, such as a camera, an RFID detector, echo-location detector, magnetic sensor, laser detector, or other sensor suitable for locating at least one of the one or more markers relative a common reference.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 6 is a perspective schematic representation of a tele-surgical system, in accordance with many embodiments.

FIGS. 23-24 show schematics of example methods in accordance with aspects of the

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiments being described.

The kinematic linkage structures and control systems described herein are particularly beneficial in helping system users to arrange the tele-surgical manipulator structure on a particular patient. Along with actively driven manipulators used to interact with tissues and the like during treatment, tele-surgical systems may have one or more kinematic linkage systems that are configured to support and help align the manipulator structure with the surgical work site. While the high degree of configurability of these kinematic systems offer many advantages and advanced features, it can be difficult to locate a location of a manipulator feature of the manipulator assembly with respect to a separate component, such as a surgical table, particularly when the surgical table is separately positionable from the manipulator assembly. Since it is often useful to position a patient in various orientations or alignments in preparation for or during a procedure, it is desirable if the manipulator assembly can be localized with the surgical table either during initial set-up, or during a procedure, so that a position and/or orientation of the surgical table relative to the manipulator assembly can be determined and potentially utilized in calculated manipulator movements or surgical table movements (either automatic or user driven). Such localization and pose estimations methods allow further utilization of various calculated movement of the manipulators described in related applications, including but not limited to various null-space movement and collision avoidance movements, and may further be used to determine a position and/or orientation of the surgical table to any manipulator or associated component of the manipulator assembly. In addition, pose estimation may be used in accordance with various other features, such as any of those described in U.S. application Ser. No. 14/101,769 filed on Dec. 10, 2013, entitled, "Collision Avoidance During Controlled Movement of Image Capturing Device and Manipulatable Device Movable Arms," which is incorporated herein by reference in its entirety for all purposes, or any of the references incorporated by reference therein. The systems, devices and methods described herein, while applied to these particular surgical systems, may be used with various different types of manipulator systems, in accordance with the aspects of the invention described herein.

Minimally Invasive Tele-Surgery

Figure 1:
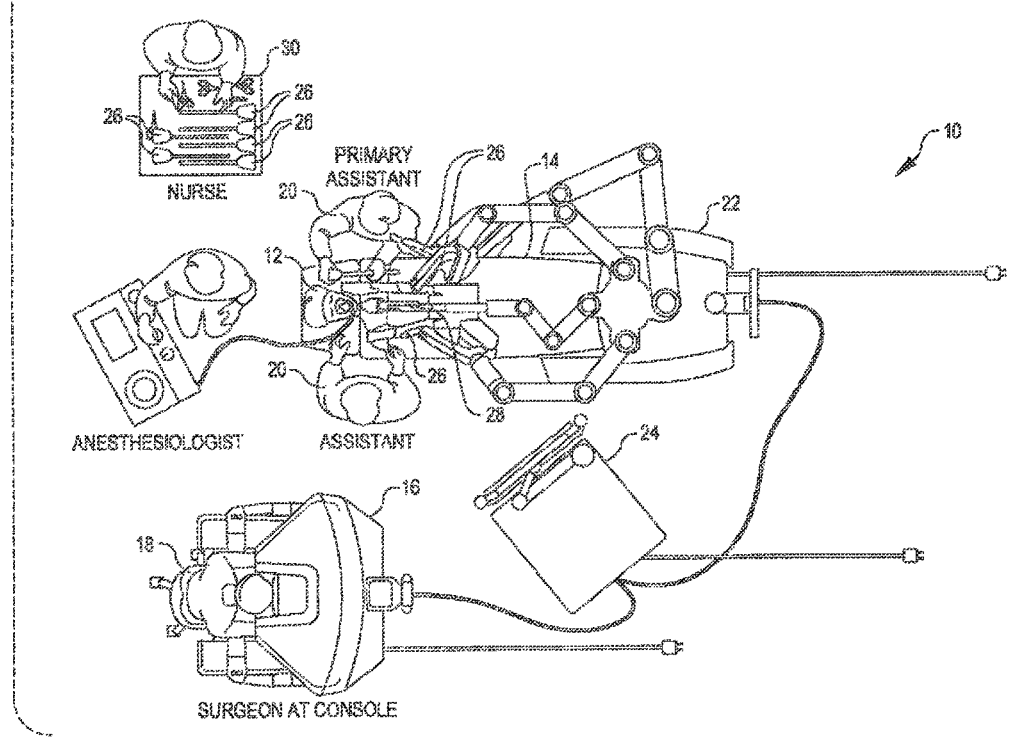
FIG. 1 is a plan view of a minimally invasive tele-surgical system being used to perform a surgery, in accordance with many embodiments.

Referring now to the drawings, in which like reference numerals represent like parts throughout the several views, FIG. 1 is a plan view illustration of a Minimally Invasive Tele-surgical (MIRS) system 10, typically used for performing a minimally invasive diagnostic or surgical procedure on a Patient 12 who is lying down on an Operating Table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
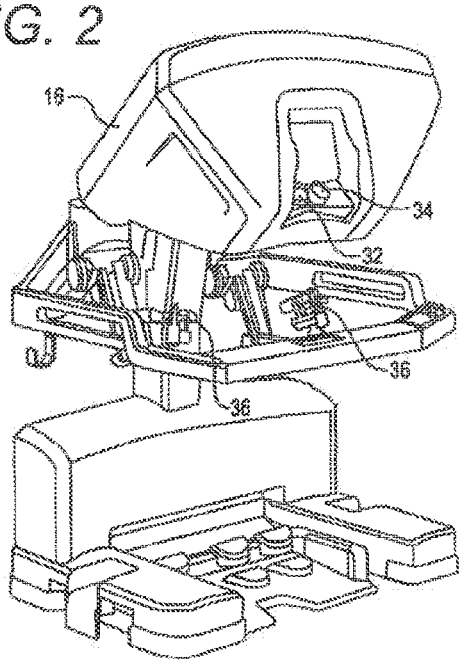
FIG. 2 is a perspective view of a surgeon's control console for a tele-surgical system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with tele-presence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
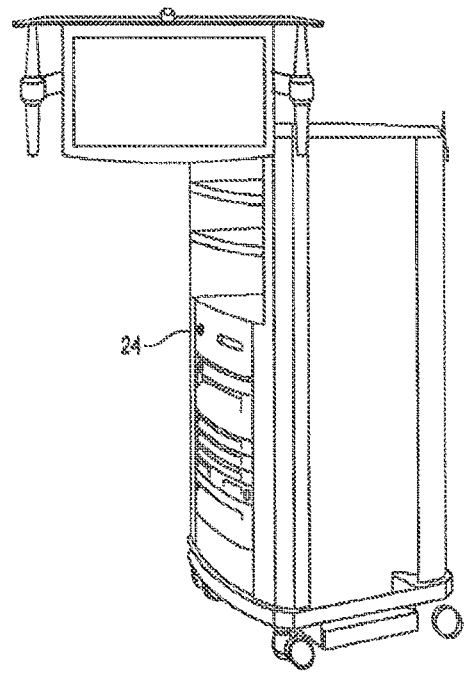
FIG. 3 is a perspective view of a tele-surgical system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
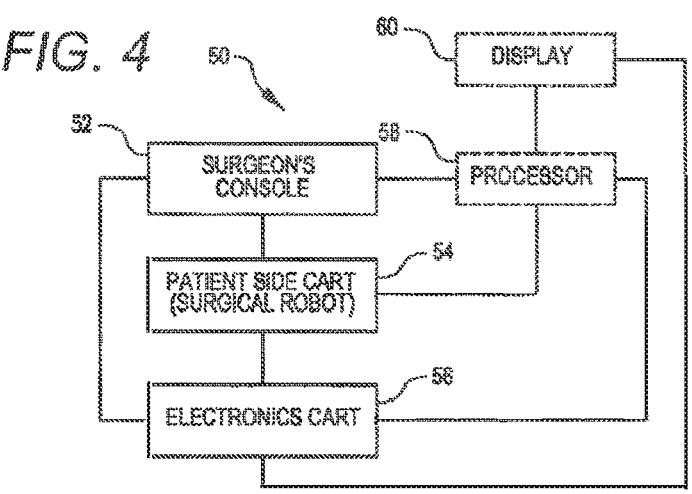
FIG. 4 diagrammatically illustrates a tele-surgical system, in accordance with many embodiments.

FIG. 4 diagrammatically illustrates a tele-surgical system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the manipulator structures described herein. The software will often comprise a non-volatile media, and could also comprise a monolithic code but will more typically comprise a number of subroutines, optionally running in any of a wide variety of distributed data processing architectures.

Figure 5A:
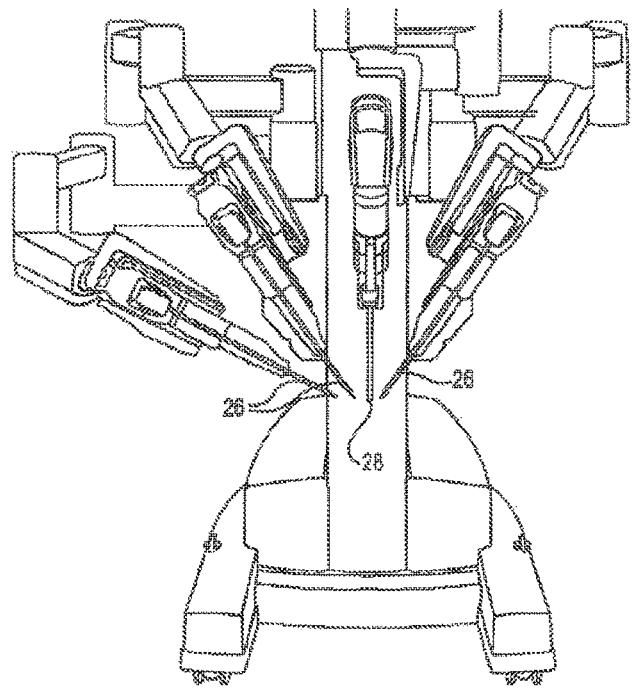
FIG. 5A is a partial view of a patient side cart (surgical robot) of a tele-surgical system, in accordance with many embodiments.
Figure 5B:
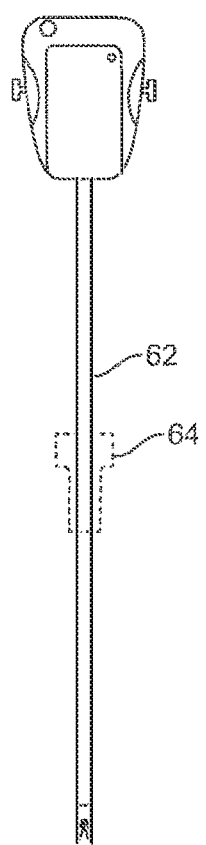
FIG. 5B is a front view of a tele-surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by manipulator mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the manipulator arm and the shaft of surgical tool 26 passes through the lumen of the cannula. The manipulator arm may transmit signals indicating that the cannula has been mounted thereon.

Tele-Surgical Systems and Modular Manipulator Supports

FIG. 6 is a perspective schematic representation of a tele-surgical system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
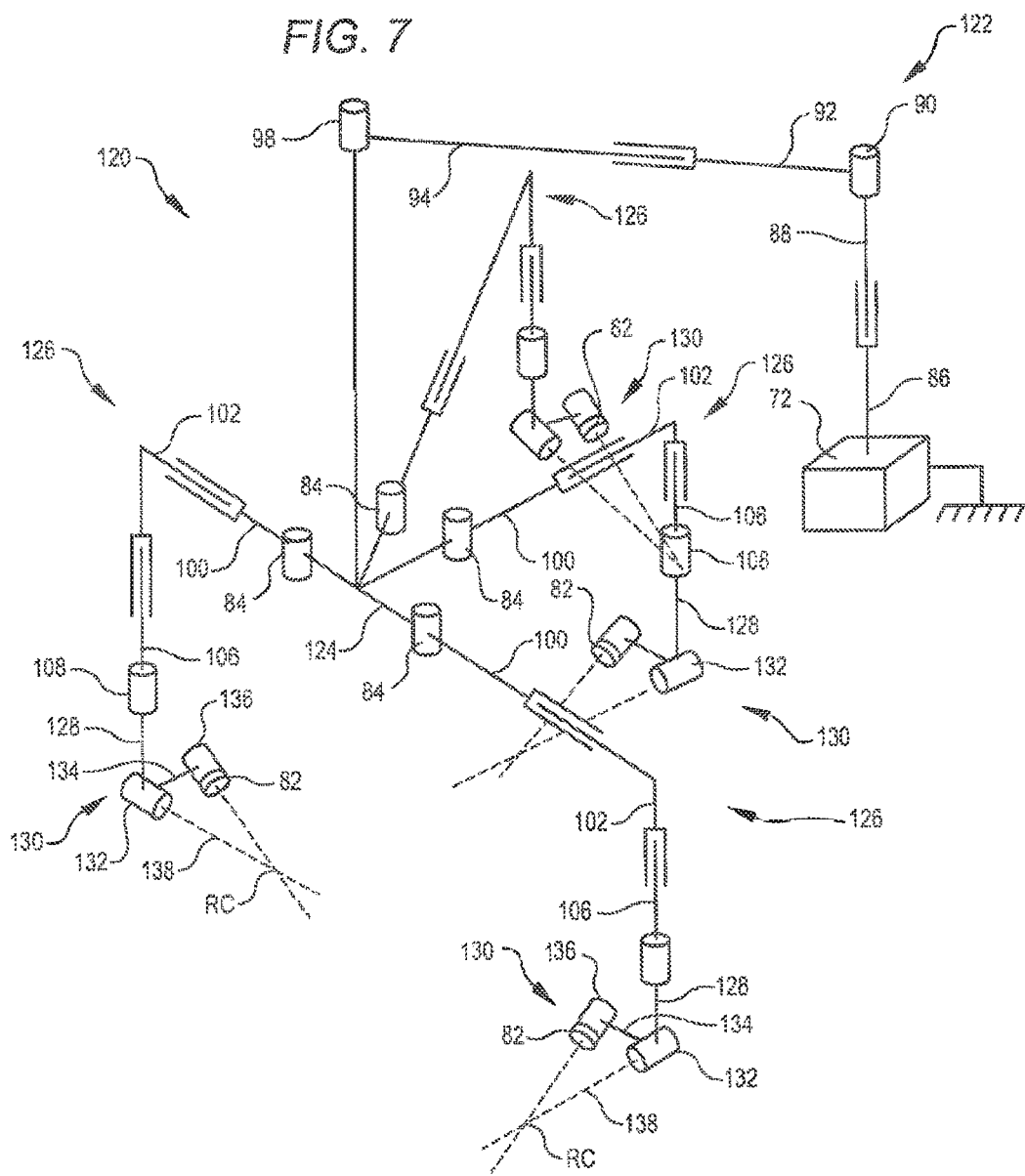
FIG. 7 is a perspective schematic representation of another tele-surgical system, in accordance with many embodiments.

FIG. 7 is a perspective schematic representation of a tele-surgical system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
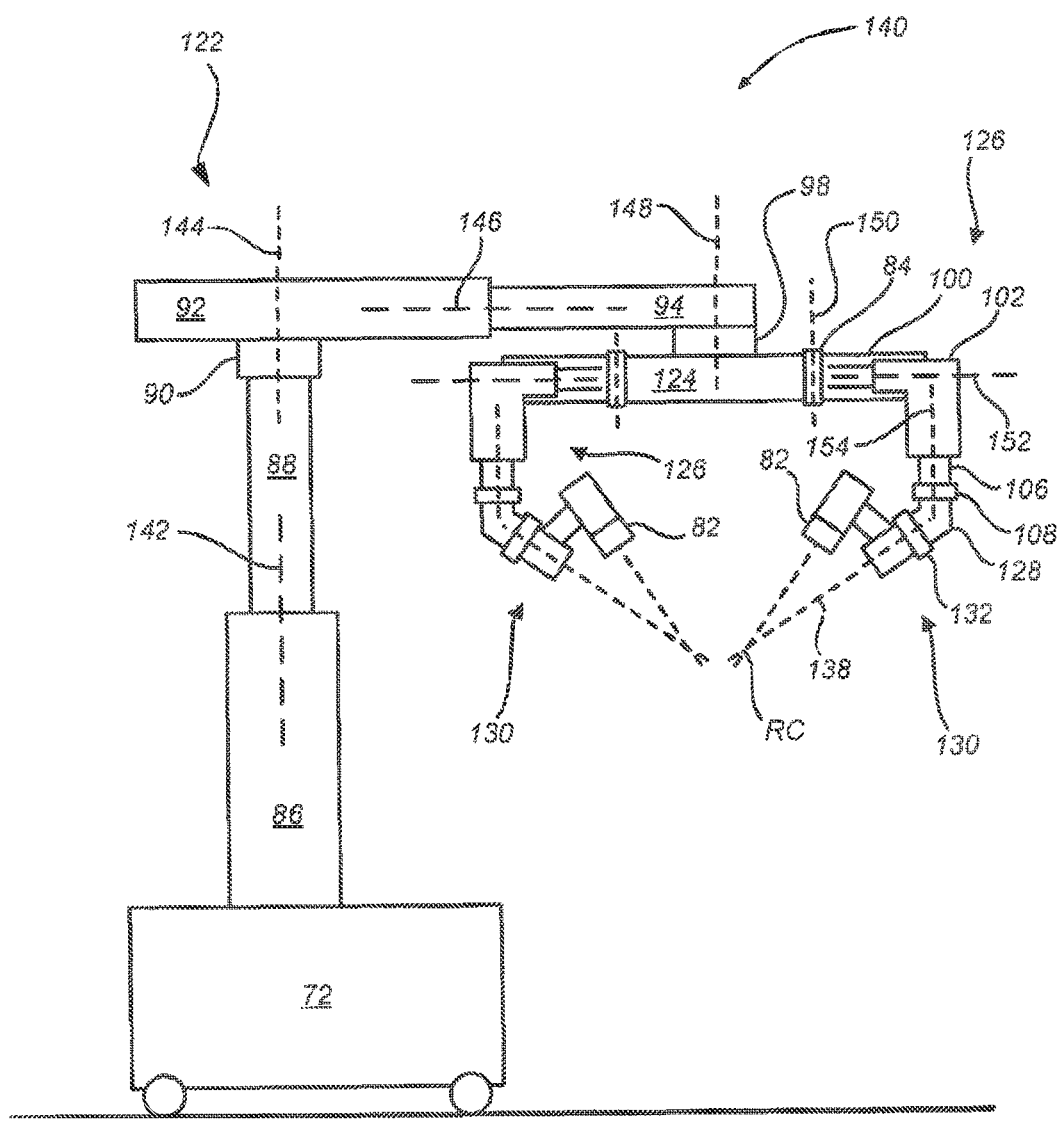
FIG. 8 shows a tele-surgical system, in accordance with many embodiments, in conformance with the schematic representation of FIG. 7.

FIG. 8 is a simplified representation of a tele-surgical system 140, in accordance with many embodiments, in conformance with the schematic representation of the tele-surgical system 120 of FIG. 7. Because the surgery system 140 conforms to the tele-surgical system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. The wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
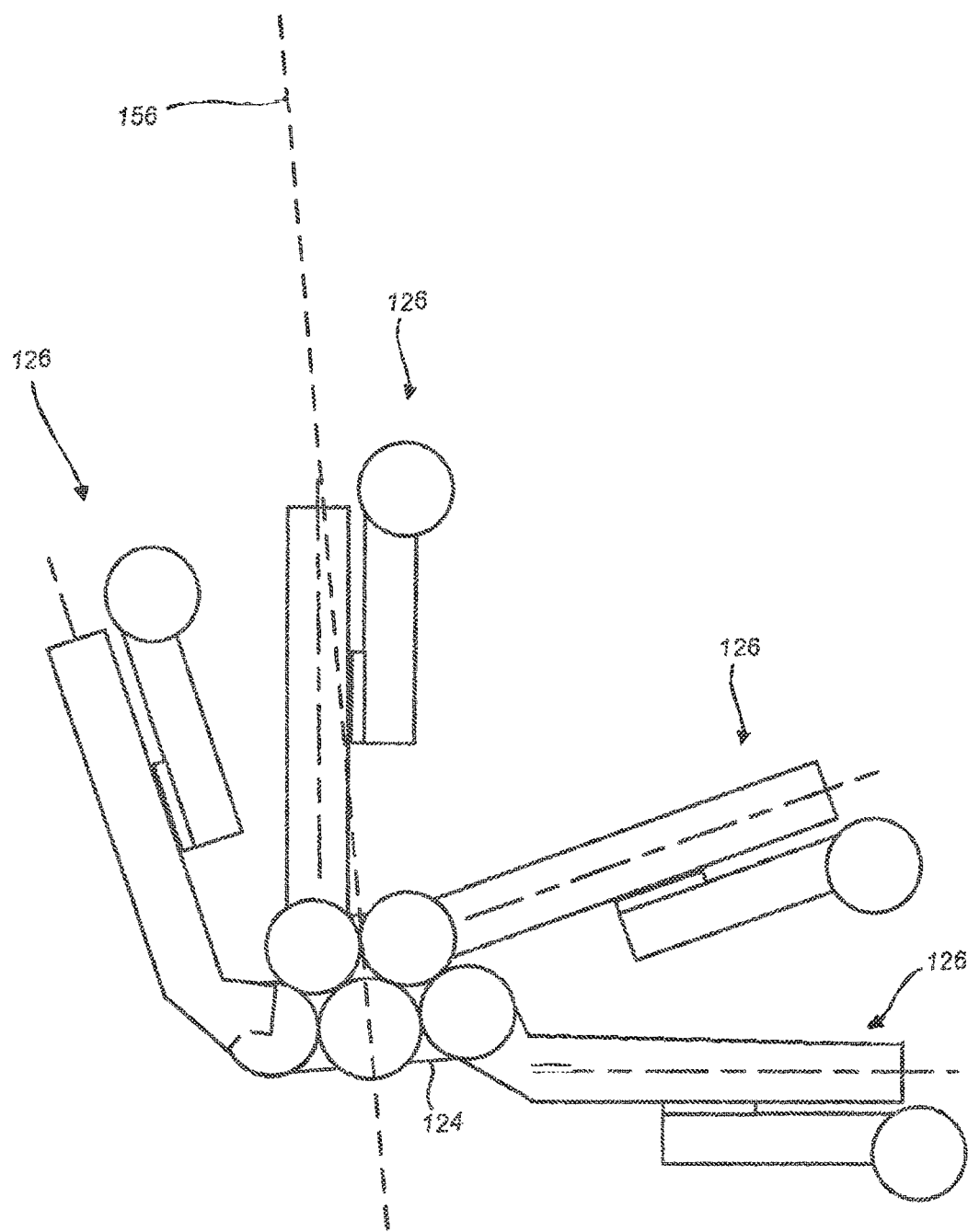
FIG. 9 illustrates rotational orientation limits of set-up linkages relative to an orienting platform of the tele-surgical system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

In use, it will often be desirable for a surgical assistant, surgeon, technical support, or other user to configure some or all of the linkages of tele-surgical system 140 for surgery, including the set-up structure linkage, the set-up joints, and/or each of the manipulators. Included among the task in configuring these linkages will be positioning the orienting platform 124 relative to first stage member 94 about vertical fourth SUS axis 148 of wrist joint 98. A joint drive motor 121 and/or brake system 123 is coupled to wrist joint 98, with one exemplary embodiment including both a drive 121 and brake 123. Additionally, a joint sensor system will typically sense an angular configuration or position of wrist joint 98.

An exemplary user interface, system, and method for manually configuring the system for use will be described herein with reference to manual articulation of orienting platform 124 by articulation of wrist joint 98 about fourth SUS axis 148, as schematically illustrated by arrow 127. It should be understood that alternative embodiments may be employed to articulate one or more alternative joints of the overall kinematic system, including one or more alternative joints of the set-up structure, one or more of the set-up joints, or one or more of the joints of the manipulators linkages. Use of the exemplary embodiment for articulating the motorized wrist joint embodiments may allow a user to efficiently position manipulators 82. The manual articulation of wrist joint 98 as described herein can improve speed and ease of use while manually docking manipulators 82 to their associated cannulas 64, as shown in FIG. 5B.

Figure 10:
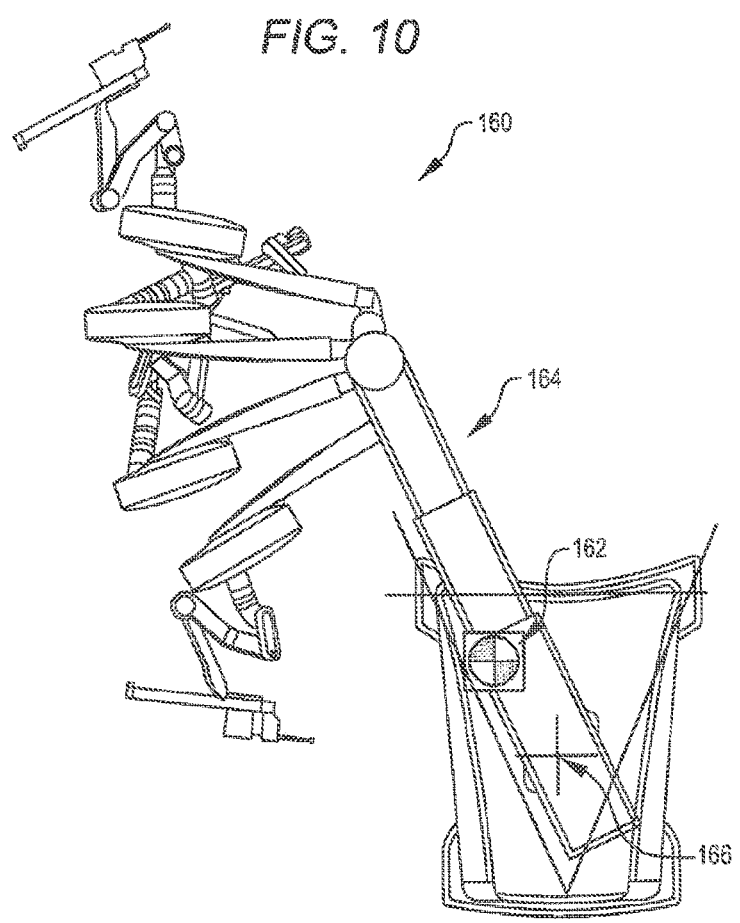
FIG. 10 shows a center of gravity diagram associated with a rotational limit of the boom assembly for a tele-surgical system, in accordance with many embodiments.

FIG. 10 shows a center of gravity diagram associated with a rotational limit of a support linkage for a tele-surgical system 160, in accordance with many embodiments. With components of the tele-surgical system 160 positioned and oriented to shift the center-of-gravity 162 of the tele-surgical system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a pre-determined stability limit of the mounting base.

Figure 11A:
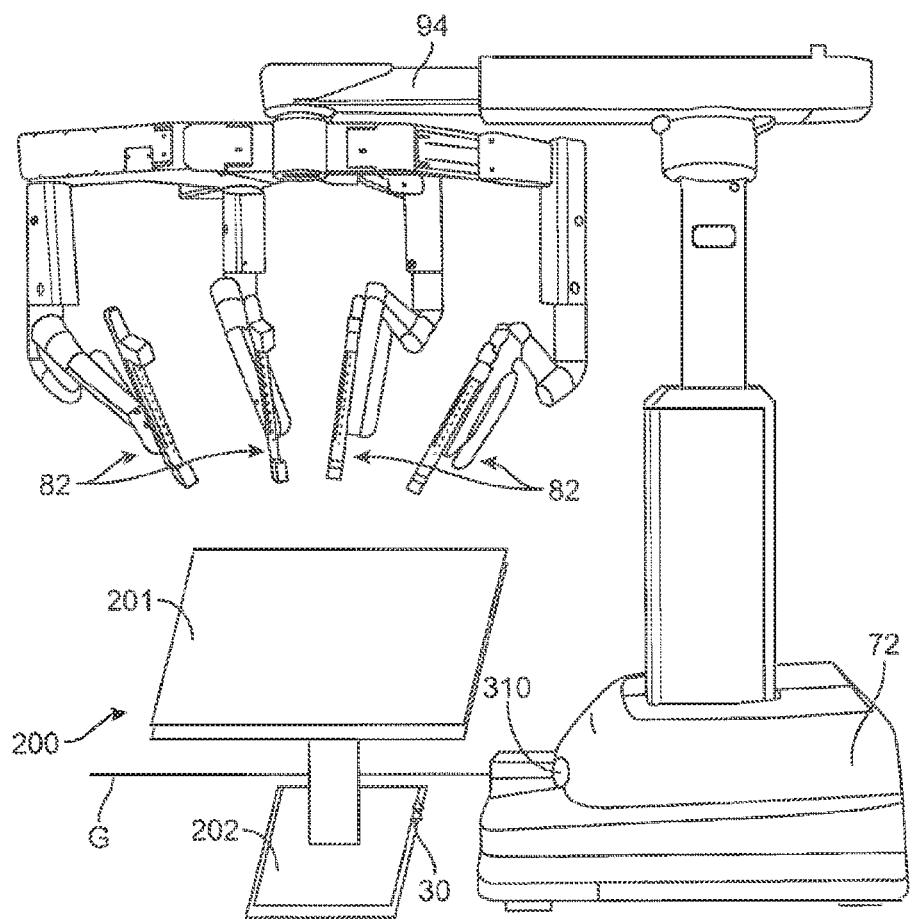
FIG. 11A shows an example manipulator assembly having a location camera and positionable surgical table having a fiducial marker, in accordance with aspects of the invention.
Figure 11B:
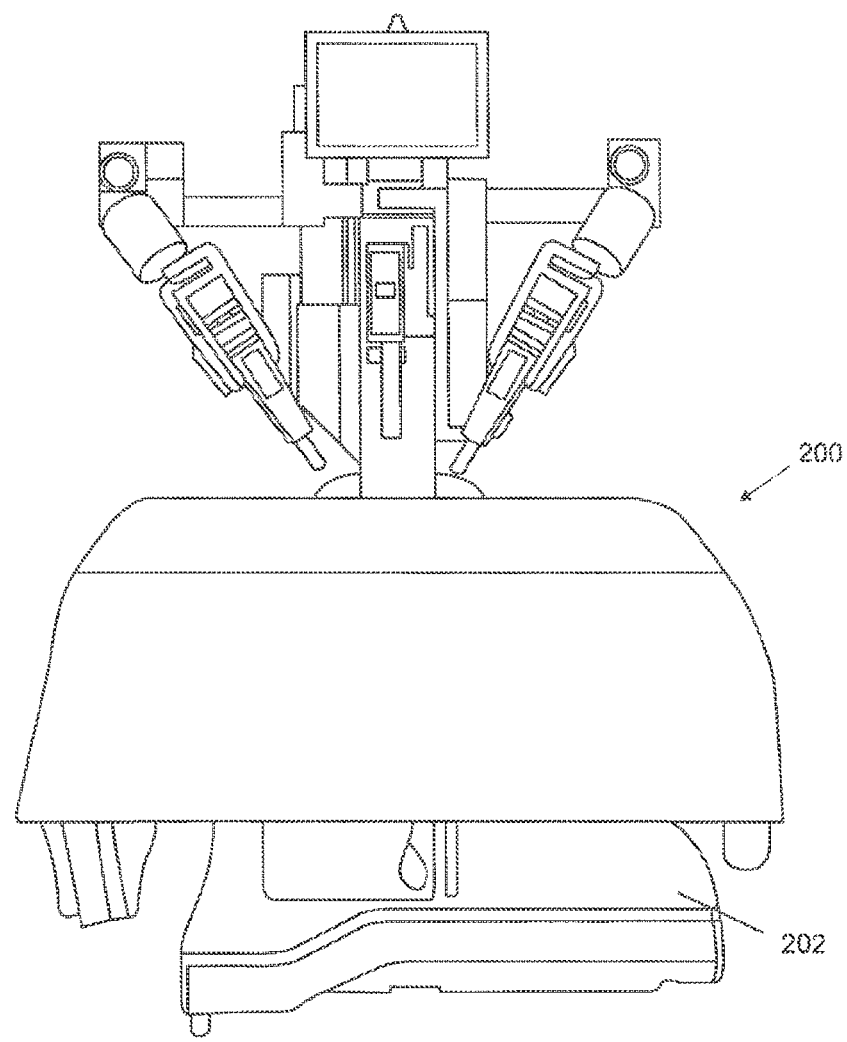
FIG. 11B shows an example manipulator assembly and positionable surgical table with a draping applied over the table, in accordance with aspects of the invention.

FIGS. 11A and 11B illustrate an overview of an example system including the Patient Side Cart 22 having multiple manipulator arms 82 supported by associated set-up structure linkages 126 under which a surgical table 200 is disposed. In certain aspects, the surgical table 200 is a separate structure from the Patient Side Cart such that the surgical table is separately positionable, and often independently positionable, from the Patient Side Cart. It is understood however, that in certain other aspects, the localization and pose estimation methods described herein allow for a separately positionable surgical table to be controlled in coordination with calculated movements of the manipulator such that the surgical table remains separately positionable but may no longer be considered independently positionable since such movements would be coordinated by the system. In many embodiments, surgical table 200 includes a surgical table patient support surface 210, supported by a support column 204 attached to a support base 202. The system further includes fiducial markers 300 that allow the system to register the surgical table relative the Patient Side Cart such that a spatial relationship between the manipulators of the Patient Side Cart and the surgical table patient surface 210 can be determined and may be utilized in calculated manipulator movements or commanded surgical table movements.

Figure 12:
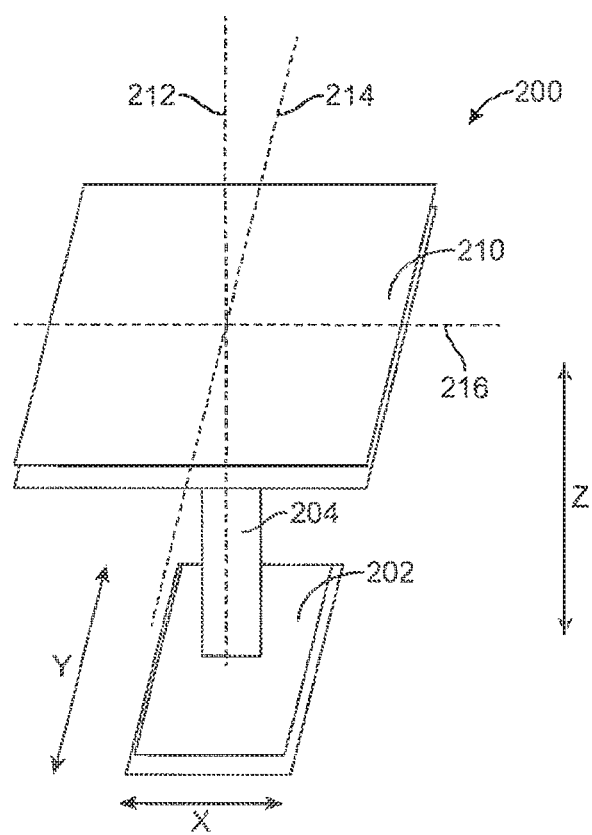
FIGS. 12 and 13A-13C show an example surgical table positionable along six degrees of freedom.

FIG. 12 illustrates an example surgical table 200 for use a surgical manipulator system. The surgical table 200 may include one or more joints (not shown) that when actuated move the surgical table top to a desired position and/or orientation. The one or more joints may include driven joints, manually articulated joints, or a combination thereof. Such joints may include translatable joints, such as hydraulics, as well as rotatable and pivotal joints, such as any of those described herein. The one or more joints may be adjusted by a patient side-assistant or anesthesiologist, as needed, or may be configured to be adjusted by a more remote user, such as a physician from the Surgeon Console, or by the system according to an autonomous algorithm or according to one or more calculated movements, such as a compensating movement for physiological movements, such as patient breathing and the like.

Figure 13A:
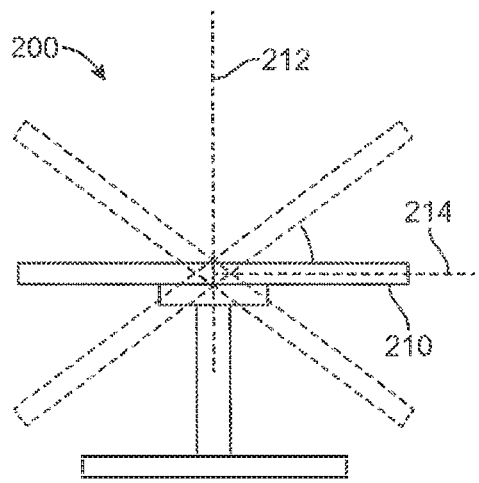
Figure 13B:
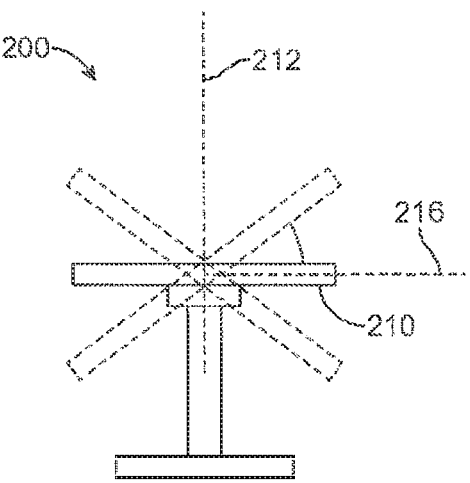
Figure 13C:
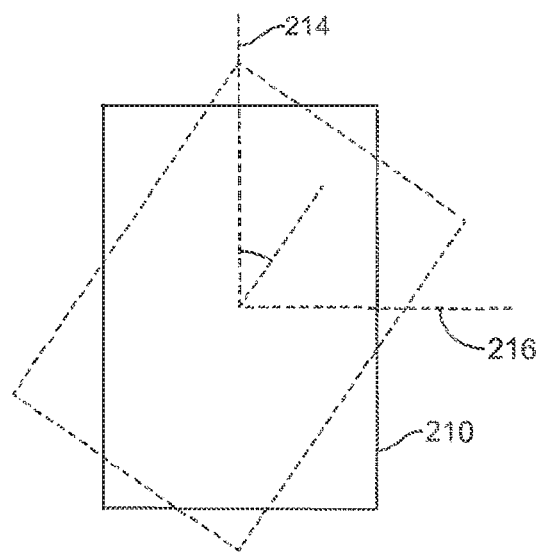

The surgical table 200 includes the surgical table patient support surface 210 supported by a support column 204 extending vertically from a support base 202. Typically, the surgical table 200 is positionable along at least one degree of freedom, preferably along multiple degrees of freedom, and even more preferably along six degrees of freedom. As shown in FIG. 12, the example surgical table 200 can be translated in three different directions orthogonal to one another, along the x-axis, the y-axis and vertically along the z-axis, and can be pivoted about axis 214 extending along the length of the patient support surface 210, pivoted about axis 216 extending along the width of the patient support surface 210 and pivoted about axis 212 extending vertically. These pivotal movements are illustrated in FIGS. 13A-13C. Thus, the example surgical table 200 is positionable along six degrees of freedom. It is appreciated that these pivotal axes do not necessarily intersect. The various positions and/or orientations of the patient support surface 210 allowed by these six degrees of freedom may be utilized during initial set-up to achieve a desired position, orientation or inclination of the patent or may be utilized during a procedure as needed to reposition the patient for any reason. It is appreciated that the pivotal movements need not be centered along those particular axes shown, such that a table may provide such pivotal movements along various other axes in the same directions, thereby allowing the surgical table top to provide pivotal movements about various locations on or off the table top. In some embodiments, the surgical table is configured to provide such movements about an isocenter at or near a cannula through which an instrument is inserted within a minimally invasive aperture.

While the high degree of configurability of such a surgical table provides many advantages and versatility in positioning the patient, this configurability can further pose additional challenges in calculating movements of the manipulator arms and associated tools. For example, when the surgical table is positioned at an incline, certain movements of the tool or an associated manipulator supporting the tool may collide with the patient support surface. While various methods may be used to avoid such collisions, it is particularly useful if the position of the surgical table relative the manipulators of the Patient Side Cart is determined so that movements of the manipulators can be calculated to account for the position of the surgical table and/or to compensate for movement and/or repositioning of the surgical table during a procedure. To allow such a determination, methods and systems in accordance with aspects of the present invention provides a table pose estimate of the surgical table relative the Patient Side Cart so that a spatial relationship between the surgical table and Patient Side Cart can be determined and utilized in various calculated movements as needed. In another aspect, methods of the invention may be used to identify a surgical table for use with a particular manipulator assembly and/or establish communication with the surgical table to allow various calculated coordinated movements therebetween.

In one aspect, the relative pose of the operating table and the robot is needed since both the robot and the table is articulated object with multiple degrees of freedom. By determining the pose of the surgical table relative the manipulator assembly, various advantageous features can be realized by performing coordinated movements between the surgical table and the manipulator assembly. Since the DOFs of each of the surgical table and the manipulator assembly can be sensed through sensors, determination of a relative pose between any two parts of the component is sufficient. In one aspect, the methods determine position and orientation of a base of the surgical table, which allows the system to determine relative positions of the various components of each of the surgical table and the manipulator assembly relative to one another.

In certain embodiments, the table is controlled to rotate around the centroid of the ports in order to minimize the overall motion of the ports (isocenter concept). This is useful for various features and in particular, "port dragging." If the port dragging results in too much force to patient's body wall active driving of the robot arms is needed to follow the motion of the table. The knowledge of the patient placement (through table placement) with respect to the robot helps the robot to optimize its control to avoid potential collision with the patient. There are multiple ways of measure a relative pose between two objects. There are several constraints that make us to choose optical solution as a preferred method.

In certain aspect, methods of the present invention provide various advantageous features over conventional manipulator systems. In one aspect, the methods include determining 6 DOF 3D pose (translation and rotation) between the surgical robot and the operating table using a camera mounted on the robot and fiducial markers on the external surface of the operating table. The 3D pose becomes 3 DOF 2D pose on the ground plane both components are assumed to be located on a common ground plane. The fiducial marker can be sub-divided into components that can be independently recognized and identified, or a subset of the fiducial marker can be recognized and identified against the entire marker. The fiducial marker embeds redundancy such as check sum or Reed-Solomon error checking and correction scheme. In certain aspects, the fiducial marker contains visual features that can be accurately localized in an image for use in pose estimation. The fiducial marker may consist of multiple unique 2D barcodes which can be data matrix codes. The fiducial markers may consist of multiple unique 1D barcodes with the bars in vertical orientation. In another aspect, the fiducial marker may consist of multiple single point light emitting devices in a blinking pattern (e.g. Morse code), and may also be combined with color to form unique identifiers of the devices.

It is appreciated that embodiments may include one or more markers that include aspects of any of the fiducial markers described herein. For example, a table may include one or more markers that include 1D, 2D or 3D barcodes in combination with light emitting device, RFID tags, or any aspect described herein. In addition, such markers may be included on various differing locations on the table so as to allow sensing of the respective markers by one or more corresponding sensors associated with one or more other external devices. In is further appreciated that the methods of localizing a table relative a manipulator assembly apply to non-surgical applications, for example in simulation, testing and/or setup of tele-surgical system, as well as in various other applications, including but not limited to various industrial robotic applications.

In certain other aspects, the fiducial marker can be used to identify a type, model, serial number of a surgical table being used with a particular manipulator assembly. The marker pattern may include a unique identifier for each operating table. The software can be configured to detect the fiducial markers in the image, extracts the locations of the visual features. The unique identifications of the fiducial markers allowed correspondence to be established by using of known 3D locations of the markers. The corresponding 3D and 2D observations are used to compute the 3D pose of the operating table with respect to the camera. In certain embodiments, multiple surgical robots or disjoint surgical robot components each equipped with a camera. In one aspect, the relative poses are computed by having the cameras to observe a common operating table with fiducial markers on its external surface. It is appreciated that the cameras are not required to have a common view. Among the many advantages of these methods, is that, in many embodiments, a physical connection between the manipulator assembly and the operating room table is not required for localization. As long as line of sight is maintained between the sensor associated with the manipulator and the at least one marker pattern of the surgical table, localization is not affected by the environment (e.g. EMI). In some aspects, once localization is established line of sight need not be maintained unless the table is repositioned. In another aspect, a movable support structure which the table top is positioned wirelessly communicates with the manipulator assembly such that any changes in table pose after localization are accounted for without requiring the table be re-localized using the one or more fiducial markers.

Figure 14A:
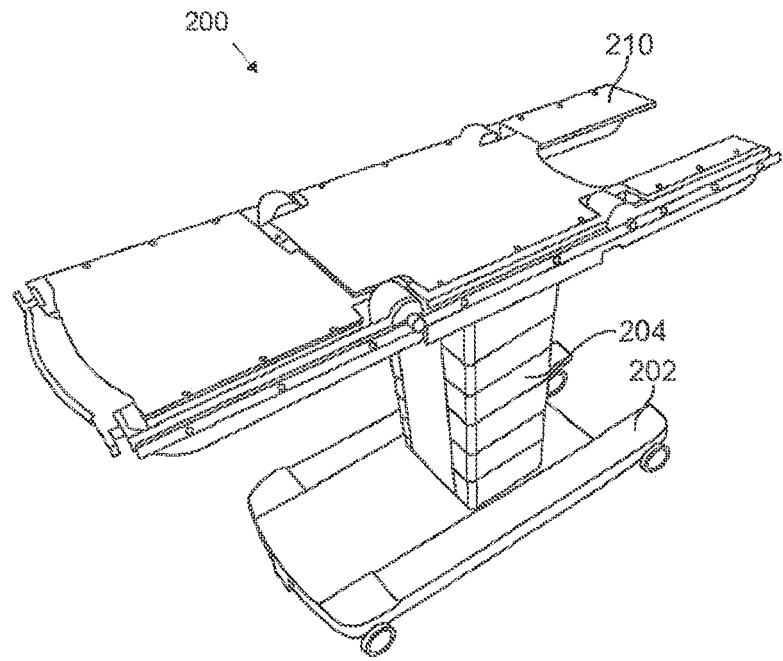
FIGS. 14A-14B show an example surgical table having a base with fiducial markers, in accordance with aspect of the invention.
Figure 14B:
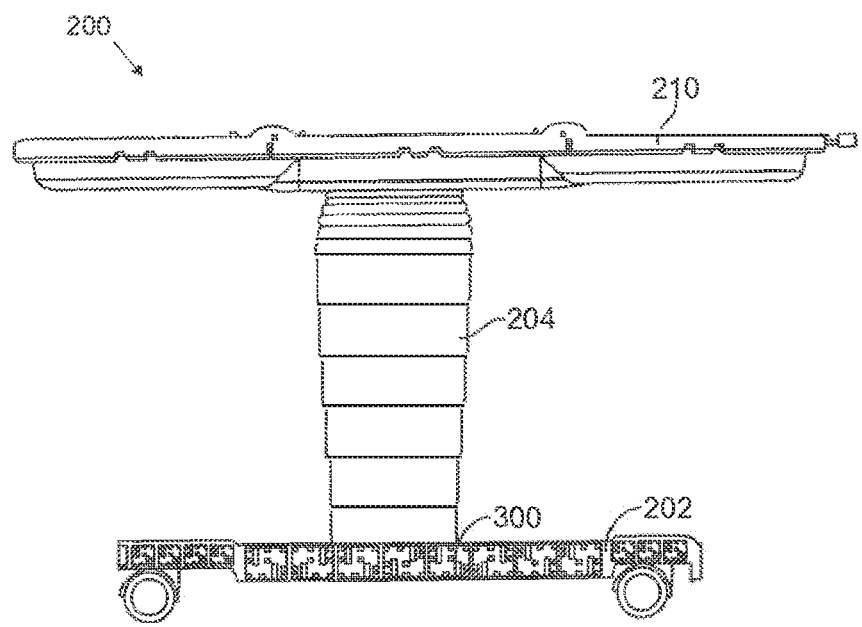

FIGS. 14A-14B shows example surgical tables in accordance with aspects of the present invention. Each shows a positionable surgical table 200 having a patient support surface 210, vertical support column 204 and a movable support base 202 having fiducial markers 300 thereon. In one aspect, the base is metal and the fiducial markers are laser etched, engraved, or embossed on the surgical table, for example on a base or a side of a table top substrate. This method of producing the fiducial markers is advantageous as it is easily sterilizable, as opposed to various other types of markers. In addition, such markers are not easily removed such the marker can be used to ensure proper identification of the surgical table for use with a particular manipulator assembly.

Figure 15:
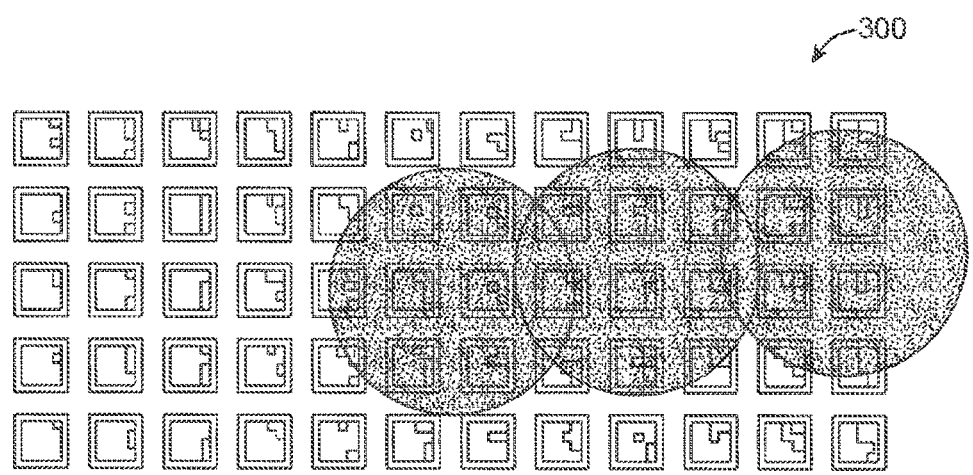
FIG. 15 shows a detail example of the fiducial markers shown in FIG. 14B.
Figure 16:
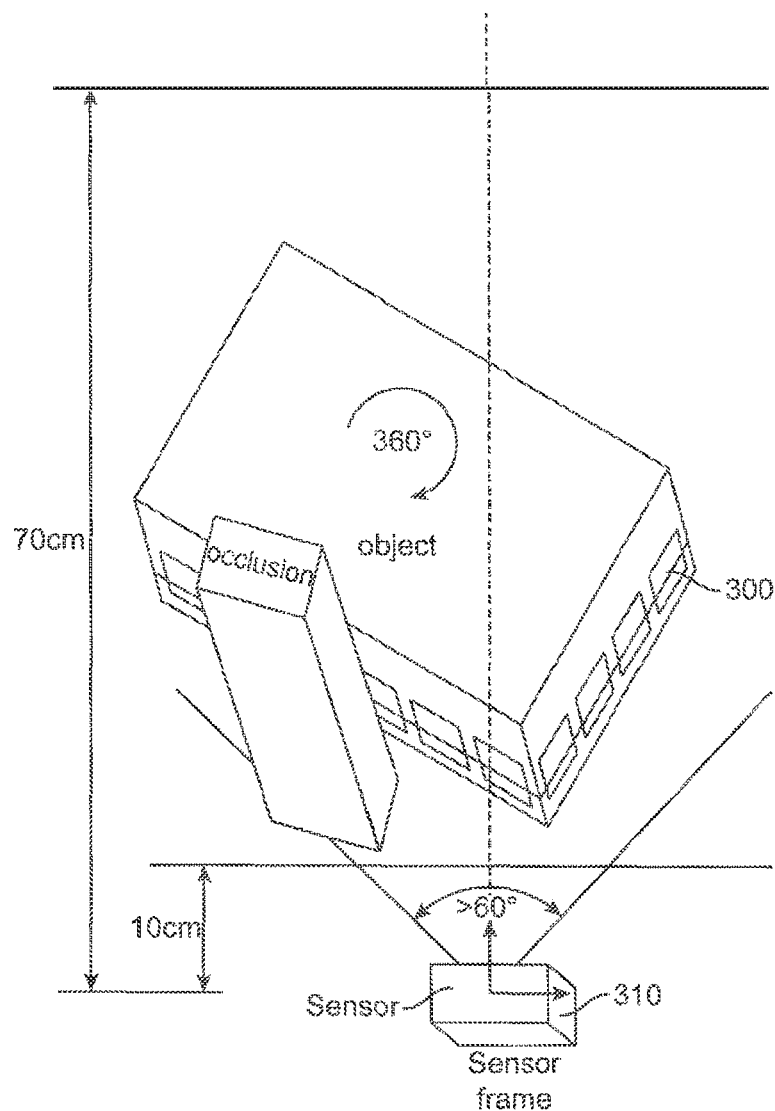
FIG. 16 shows a schematic of location of an object having fiducial markers with a sensor, in accordance with aspects of the invention.

FIG. 15 shows a detail example of the fiducial markers shown in FIG. 14B. Such markers may also include 3D features such that a distance of the markers from the sensor associated with the manipulator assembly (typically a sensor or camera disposed in the base of the manipulator assembly) can be determined. In addition, the distance can also be determined by how the size and quantity of markers that are read within the reading zone of the sensor reader (indicated as circles in FIG. 15). In one aspect the marker may be any marker type suitable for determine a relative position and/or orientation of the surgical base relative the manipulator assembly. Typically, the marker scheme and sensor module are configured to estimate the 2D pose of an object on the ground using markers attached on the object. In one aspect, the markers contain error checking redundancy, such as that provided by barcodes. Durable label material are preferred that can sustain cleaning chemicals. Marker can be configured as a unique table ID as part of machine readable marker. In certain embodiments, the marker generally is between 2 cm to 12 cm in height and width and may include a series of markers along a surface of the base of the table, often around the entire table In one aspect, the marker is configured so that the marker is visible within a horizontal field of view of greater than or equal to 60 degrees such that the marker can be read by a sensor in the base of the manipulator assembly in various different positions and/or orientation. These aspects can be understood further by reference to the schematic in FIG. 16.

In one aspect, the marker and sensor are configured according to various range of motion considerations, including any or all of:

Sensor module performs pose estimation when the distance between the sensor the front of the object is in the range from 5 cm to 100 cm. It should be noted that sensor module may be configured to work when the object is either in the center or off the center of the field of the view of the sensor.

Sensor module working in extended range. Sensor module is configured to perform pose estimation when the object is of any angle to the sensor.

In one aspect, the marker and sensor are configured according to various illumination considerations including any or all of:

The environment can be from very low light (5 lux) to bright operating theatre lighting (2000 lux).

Extra illumination, if needed, can be located close to the sensor, possibly near-IR.

The extra illumination may be configured to activate, as needed, when performing image data collection.

Operating Room Table Pose Estimation

In one aspect, one distinguishing feature of manipulator assemblies that benefit from these methods is the ability of moving the patient table during the procedure without undocking and re-docking. To accommodate intra-operative table motion, an operating room (OR) table that pivots around a point in 3D can be used. In some embodiments, the pivoting point coincides with the centroid of all the ports so that the overall displacement of all ports is minimized. This may require that the relative pose of the Patient Side Cart (PSC) and the OR table to be known. Since on both the PSC and the OR table the full kinematics information is available, the pose between any part on PSC and any part on OR table is sufficient. These method address various problems that may be associated with conventional marker reading techniques or localization methods, including any or all of: no mechanical link between OR table and PSC; no cable between OR table and PSC. These methods address difficulties associated with OR environments, including low illumination associated with robotic surgery which does not require light, standard operating rooms that are particularly bright, possible interference, cautery noise, the presence of IR links and/or RF links.

In one aspect, the markers and sensor are configured to provide sufficient accuracy. In some embodiments, the accuracy requirement is that the center of the table is measured within +/−10mm, this requirement is largely derived from the size of a cannula. Even when the error is zero, since the manipulators have some displacement at each port (e.g. pivoting point is the centroid of all ports); thus, a bigger error may be tolerated.

Figure 17:
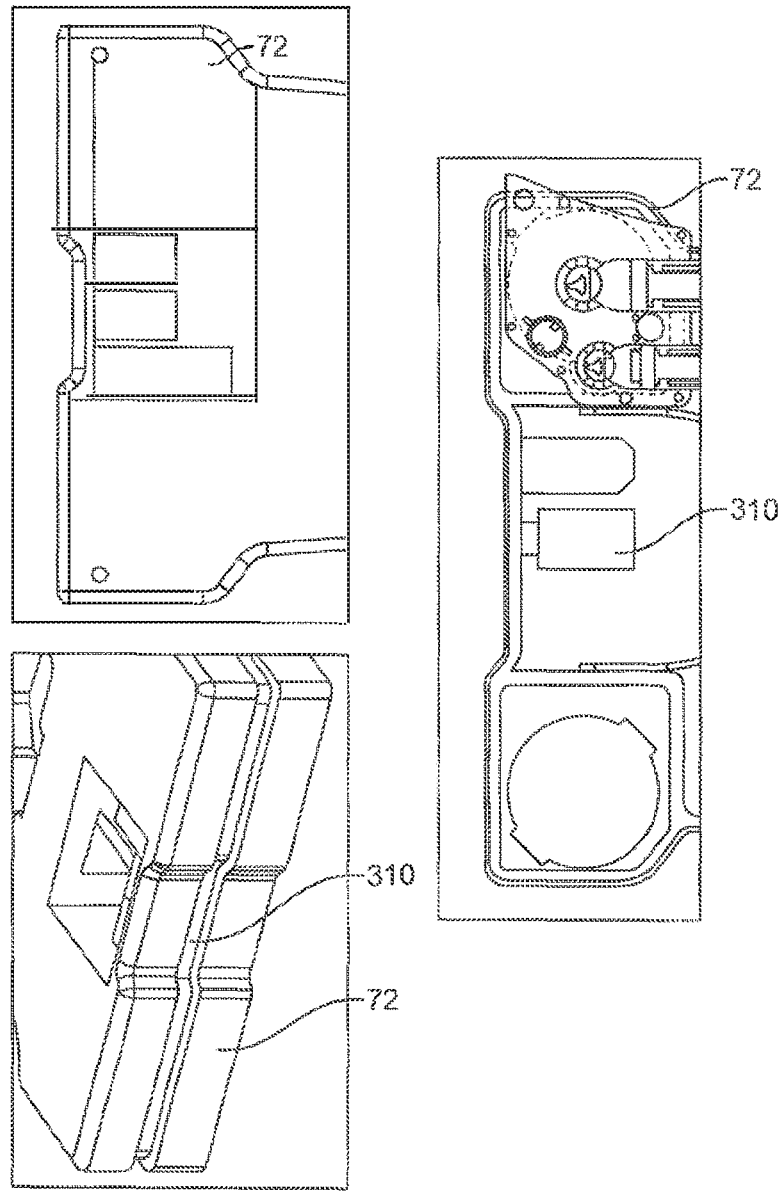
FIG. 17 show views of a camera sensor for reading of fiducial markers within a proximal base of the manipulator assembly, in accordance with aspects of the invention.

In another aspect, the sensor module needs to fit in the allocated space in the PSC base. In some embodiments, the space allotted for the sensor module in the base of the manipulator assembly is about 3"×3"×5" while the distance from the optical window to the most front surface is about 2". FIG. 17 illustrates one possible placement of a sensor camera within the base of the manipulator assembly. In some embodiments, a shock absorption is included in the sensor or camera mount.

In another aspect, the sensor and marker configuration is configured to be read so as to allow sufficient working distance between the surgical table and the manipulator assembly, which allows a range of positions and/or orientations of the surgical table. For example, the marker and sensor can be configured such that the marker can be read within a horizontal field of view of close to 60 degrees and the working distance for reading the marker may be between an inch to 2 feet or more. The table may also include markers on each side of the support base so that the table can rotated completely, as may be needed for a particular procedure.

In certain aspects, the marker and sensor may be configured to track the one or more markers with any or all of electro-magnetic tracking, optical tracking, laser based, shape sensor, ultrasonic means, or any combination thereof. Due to drawbacks associated with certain of these approaches, however, methods typically utilize optical tracking of markers to perform pose estimate as described herein. One benefit is optical tracking is that it is not affected by invisible interference (e.g. electromagnetic (EM) interference). A down side is the line of sight issue since the fiducial markers need to be visible. However, different to EM interference, this is much easier for the user to understand to correct (e.g., moving away a trash can between the camera and the marker). The basic principal of the optical tracking is to compute the pose of an object or fiducial marker with known geometry by its image observations. In another aspect, a monocular or a pair of stereo cameras can be used.

In one aspect, multiple passive retro-reflective balls or active blinking LEDs forming a geometrically unique configuration. In one aspect the fiducial marker comprise 2D barcodes. Any 2D barcode should be able to be used as marker as long as the reader can provide the image coordinates of the some reference points (ideally>=4) of the barcode. In another aspect, active point markers may be used. Multiple active point markers (e.g. LEDs) are placed around the peripheral of the table base. Their blinking patterns are unique to make them easily self-identifiable. If >=3 points are visible in the view, pose can be computed. Since it is an emitting fiducial, the contrast is higher than passive marker and there is no light source needed on the PSC. The overall power consumption for illumination is much lower. Unlike the passive makers, it requires the makers to be powered and controlled, which makes it less desirable. It is possible to use an ld CCD sensor if all the fiducial markers are on the same level.

Optical Pose Estimation

Figure 18B:
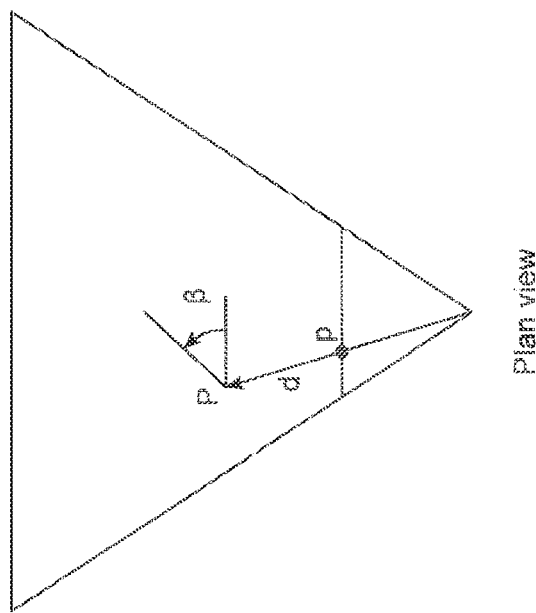
FIGS. 18A-18B show plots demonstrating optical pose estimate based on reading of fiducial markers, in accordance with aspects of the invention.
Figure 18A:
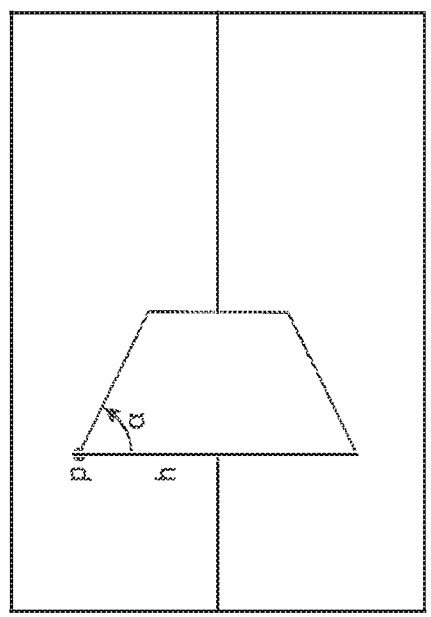

FIGS. 18A-18B show plots illustrating pose estimation with optical tracking. The plots above show the theory of pose estimation in a simplified setup where the camera center is at the enter of the pattern and camera looks horizontally. The pattern in the image should be mirrored by the horizon therefore only the upper part is considered. The x coordinate of p determines its angle of the ray in plan view.

They coordinate of p (h) determines the distance (d). The 3D rotation of the marker has a 1:1 mapping with the image rotation of the trapezoid side. These three quantities in the image can fully determine the 3 DOF pose in plan view. In this example, there are 8 measurements (4 coordinates in image). This is an over-determined system and the rest of the measurements are used to make the estimate more accurate.

The equation for such estimate is:

$$d = (H*t)I h$$

where H is the physical half height of the marker, f is the focal length in pixels (f=(resolution/2) I tan(fov12)). It is obvious that the relationship between h and d is non-linear. (As comparison, an overhead camera provides straight linear relationship and maximized utilization of image resolution). The depth resolution can be calculated by derivative of d with respect to h.

$$d' = -H*f/(h''2)$$

Figure 19A:
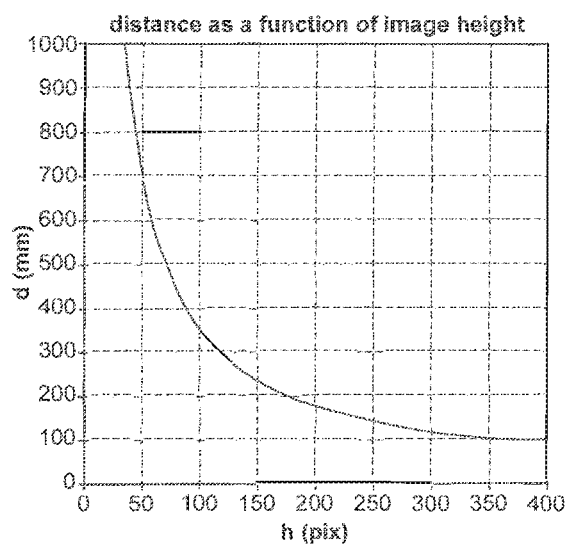
FIGS. 19A-19B show plots illustrating the accuracy of pose estimation methods, in accordance with aspects of the invention.
Figure 19B:
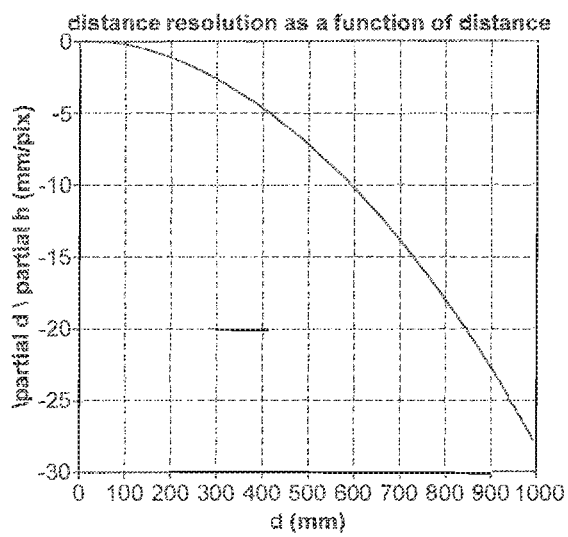
Figure 20:
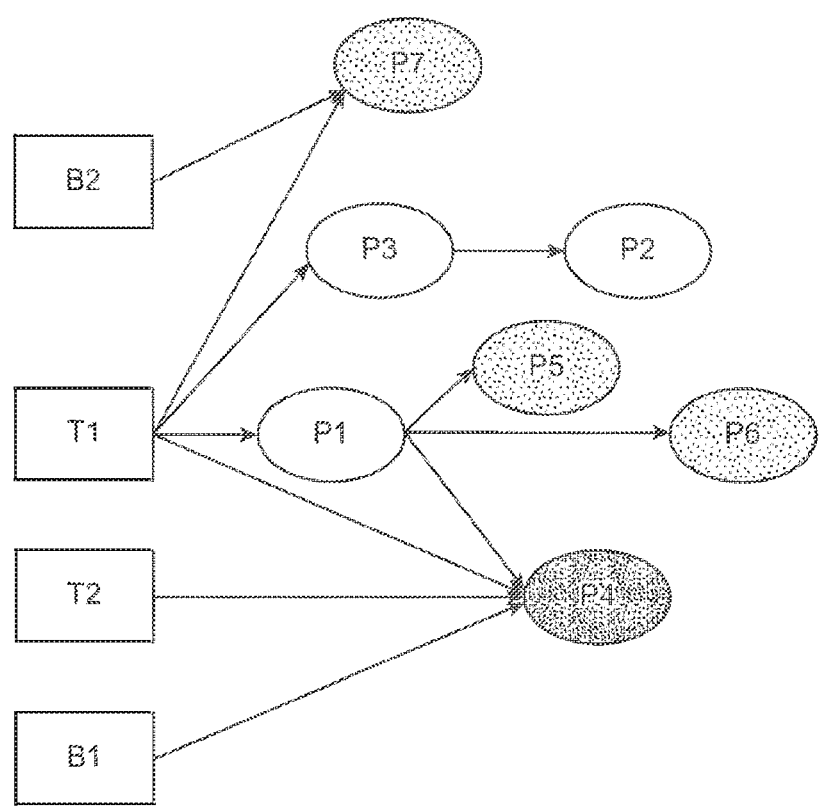
FIG. 20 shows a schematic illustrating dependencies in setting image parameters for reading of fiducial markers are variable distances with a sensor, in accordance with aspects of the invention.

The plots in FIGS. 19A-19B shows the depth resolution. In this example, the image of error of 1 pixel translates into a distance error of 10 mm at a distanced of 600 mm (~2'), roughly satisfying satisfies the accuracy requirement. In some embodiments, pose estimation includes determining the 3D pose (3 translation and 3 rotation) of an object with known geometry from a calibrated monocular camera. The module can also be in tool tracking. In another aspect, pose estimation is performed on a plane (e.g. the ground plane) such that one only needs to estimation 3 DOF (2× translation and 1× rotation). In such cases, there are at least two options:

Perform 3D pose estimation and project the 3D pose to 2D pose.

Parameterize the pose in 2D and perform optimization in 2D pose.

In some embodiments, the fiducial markers are configured to wrap around and fully cover the base of the surgical table. All areas can be covered by marker to maximize the probability of at least one is visible during a procedure. The size may be determined by the constraint of both near end and far end of the working range. The width height ratio of the barcode is designed to be greater to one due to the fact the foreshortening in horizontal direction is more than that in the vertical direction due to rotation. More quantitative analysis is provided in the next section. Self-identifiable sub-markers are one way to handle partial occlusion when the viewpoint is unknown. Each sub-marker has a unique ID and can be associated with the model. One sub-marker provides sufficient constraint for pose estimation but more submarkers improves accuracy.

In one aspect, the size of the barcodes comprises two factors. A lower limit is needed to make them detectable at the maximum distance and at the greatest rotation angle. An upper limit is needed to make sure at least a whole pattern is visible at the minimum working distance. In another aspect, the marker and sensors are configured to maintain a line of sight of the markers. As can be appreciated by reference to FIG. 11B, the surgical table is draped during a procedure such that much of the table is hidden from view. Therefore, it is particularly useful to configure the fiducial markers and sensor such that the line of sight therebetween remains unobscured when the surgical table is draped. One means by which to accomplish this is to position the fiducial markers on the base of the table and to position the sensor within the base of the manipulator assembly. It should be noted that in theory no personnel or equipment should be in between the two pieces after the system is docked. Alternatives may include infrared light, RFID tags or various other means which could potentially penetrate draping material or other such obstacles. An alternative is to include multiple sensors such that if the line of sight is blocked by one sensor, another sensor may be used.

Figure 21:
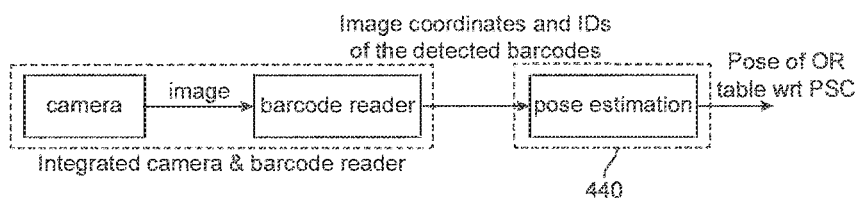
FIGS. 21-22 show schematics of pose estimate integration, in accordance with aspects of the invention.
Figure 22:
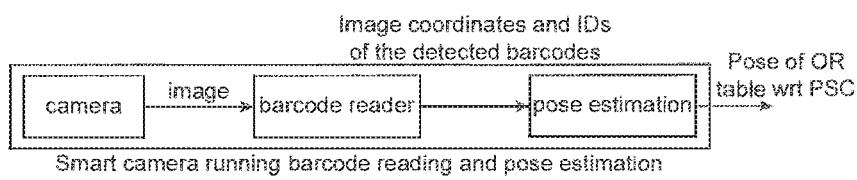

FIGS. 21 and 22 illustrate two alternative approaches that may be used in integrating the camera and barcode reader into existing tele-operation surgical manipulator systems. In one aspect, pose in the camera frame needs to be transformed into the PSC frame for it to be useful. This may include two transformations in the chain: from internal camera to camera enclosure; and from camera enclosure to PSC. In one aspect, it is particularly useful if the second can be made accurate so that calibration is unnecessary. This enables that all the calibration to be done in factory so that no field calibration is needed, in case if a camera needs to be replaced.

Figure 23:
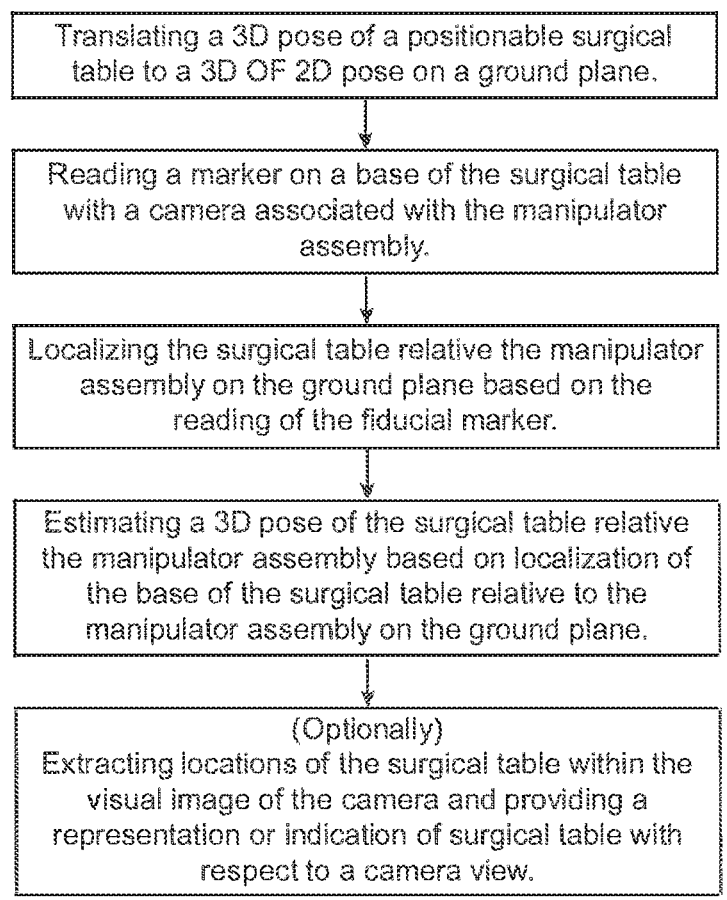
Figure 24:
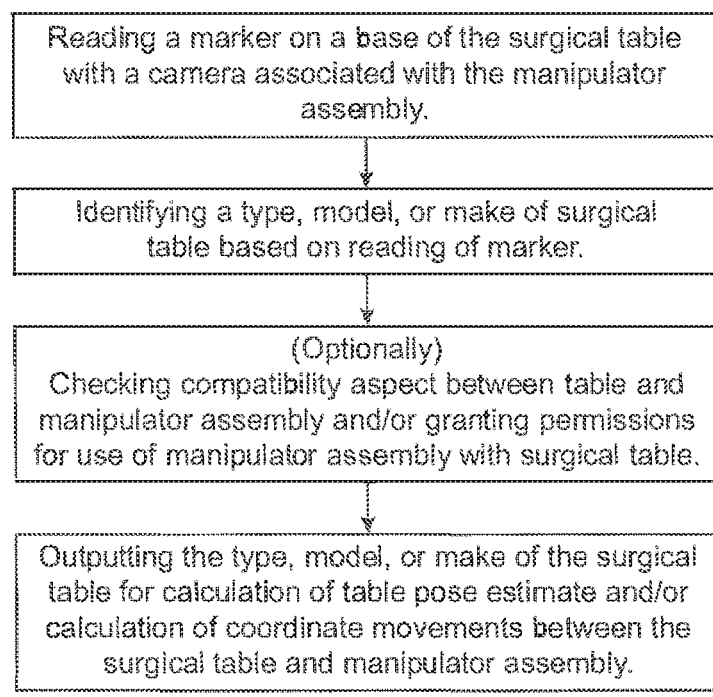

FIGS. 23-24 show example methods in accordance with aspects of the invention. In one example, methods of pose estimation include translating a 6DOF 3D pose of a positionable surgical table to a 3DOF 2D pose on a ground plane; reading a marker on a base of the surgical table with a camera associated with the manipulator assembly; localizing the surgical table relative the manipulator assembly on the ground plane based on the reading of the fiducial marker; and estimating a 3D pose of the surgical table relative the manipulator assembly based on localization of the base of the surgical table relative to the manipulator assembly on the ground plane. Some methods further include, extracting locations of the surgical table within the visual image of the camera and providing a representation or indication of surgical table with respect to a camera view. In another example, methods include: reading a marker on a base of the surgical table with a camera associated with the manipulator assembly, identifying a type, model, or make of surgical table based on reading of marker. Some methods further include: checking compatibility aspect between table and manipulator assembly and/or granting permissions for use of manipulator assembly with surgical table. Such methods may include outputting the type, model, or make of the surgical table for calculation of table pose estimate and/or calculation of coordinate movements between the surgical table and manipulator assembly.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. A method of estimating a pose of a surgical table comprising;
reading one or more fiducial markers on a base of the surgical table with a sensor associated with a manipulator assembly adjacent the surgical table, wherein the manipulator assembly supports a surgical instrument and wherein the surgical table comprises a substrate having a support surface and a support structure supporting the substrate, the support structure being movable such that the support surface is positionable along one or more degrees of freedom (DOF) and the base of the surgical table being disposed on a side of the substrate opposite the support surface; and
localizing the surgical table relative to the manipulator assembly on a common plane based on the reading of the one or more fiducial markers.

2. The method of claim 1, wherein the one or more fiducial markers are located on the surgical table at fixed locations.

3. The method of claim 1, further comprising one or more of affixing the one or more fiducial markers to the surgical table or forming the one or more fiducial markers in the surgical table at select locations in a particular orientation relative the surgical table.

4. The method of claim 3, wherein forming the one or more fiducial markers in the surgical table comprises one or more of etching, engraving, or embossing the one or more fiducial markers in the surgical table.

5. The method of claim 1, wherein reading the one or more fiducial markers comprises reading at least one of the one or more fiducial markers before and/or during a surgical procedure while a patient is supported on the surgical table.

6. The method of claim 1, wherein the common plane is a ground plane on which the surgical table and the manipulator assembly are disposed.

7. The method of claim 1, wherein the surgical table is positionable along one or more degrees of freedom (DOF).

8. The method of claim 7, further comprising translating a 6 DOF 3D pose of the surgical table to a 3DOF 2D pose on the common plane.

9. The method of claim 1, further comprising estimating a 3D pose of the surgical table relative the manipulator assembly based on localization of the surgical table relative to the manipulator assembly on the common plane.

10. The method of claim 1, further comprising extracting locations of the surgical table within a visual image obtained with a camera and providing a representation or indication of the surgical table with respect to a camera view of the camera.

11. The method of claim 1, further comprising identifying one or more of a type, model, or make of the surgical table based on reading of the one or more fiducial markers.

12. The method of claim 11, further comprising checking a compatibility aspect between the surgical table and the manipulator assembly and/or granting permissions for use of the manipulator assembly with the surgical table.

13. The method of claim 1, wherein the one or more fiducial markers are disposed at multiple locations on the surgical table.

14. The method of claim 13, wherein reading the one or more fiducial markers comprises reading a single marker of the one or more fiducial markers and wherein localization of the surgical table is based on the reading of the single marker.

15. The method of claim 13, further comprising reading at least one of the one or more fiducial markers subsequent to the initial reading of the one or more fiducial markers and localization based on the initial reading; and localizing the surgical table relative to the manipulator assembly on the common plane based on the subsequent reading of the one or more fiducial markers so as to update and/or verify initial localization.

* * * * *